United States Patent [19]

Fredenburgh et al.

[11] Patent Number: 5,424,432
[45] Date of Patent: Jun. 13, 1995

[54] PROCESS FOR THE PREPARATION OF IMIDAZOLUTIDINE

[75] Inventors: Laura E. Fredenburgh, Bayonne; Robert D. Larsen, Bridgewater; Ji Liu, Edison; Robert A. Reamer, Bloomfield; Chris H. Senanayake, North Brunswick; Thomas R. Verhoeven, Cranford, all of N.J.

[73] Assignee: Merck & Co., Inc., Rahway, N.J.

[21] Appl. No.: 249,425

[22] Filed: May 26, 1994

[51] Int. Cl.$^6$ .......................................... C07D 471/04
[52] U.S. Cl. .................................................. 546/118
[58] Field of Search ........................................ 546/118

[56] References Cited

PUBLICATIONS

Hofmann, Ger., 1981, 14, 2725.
Hofmann, Ber., 1885, 18, 2734.
Loudon, G. M.; Parham, M. E., 1978, 437.
Waki, M.; Kitajima, Y.; Izumiya, N., Synthesis 1981, 266.
Pallai, P.; Goodman, M., J. Chem. Soc., Chem. Commun., 1982, 280.
Squadrini, F.; Verdini, A.S.; Viscomi, G.C., Gazz. Chim Ital., 1984, 114, 25.
Fuller, W. D.; Goodman, M.; Verlander, M. S., J. Am. Chem. Soc., 1985, 107, 5821.
Shimonihashi, Y..; Kodama, H.; Waki, M.; Costa, T., Chem. Lett. 1988, 1821.
Wallis, E. S.; Lane, J. F., Org. Reactions 1946, 3, , Chapter 7, 267, entitled "The Hofmann Reaction".
Moriarty, M. R.; Chany II, J. C.; Vaid, R. K.; Prakash, O.; Tuladhar, S. M., J. Org. Chem. 1993, 58, 2482.
Baumgarten, H. E.; Smith, H. L.; Staklis, A., J. Org. Chem. 1975, 40, 3554.
Kajigaeshi, S.; Asano, K.; Fujasaki, S.; Kakinami, T.; Okamoto, T., Chem. Lett. 1989, 463.
Jew, S. S.; Park, H. G.; Park, H. J.; Park, M. S.; Cho, Y. S., Tetrahedron Lett. 1990, 31, 1559.
Auerbach, J.; Weissman, S. A.; Blacklock, T. J.; Angeles, M. R.; Hoogsteen, K., Tetrahedron Lett. 1993, 34, 931.
Clarke, H. T.; Behr, L. D., Org. Synth., Coll. vol. 2, 1943, 19.
Middleton, W. R.; Wibberely, D. G., J. Heterocyclic Chem., 1980, 17, 1757.
Bukowski, L.; Janowiec, M., Pharmazie, 1988, 43 (H.5), 315.
Duncia, J. V.; Carini, D. J.; Chiu, A. T.; Johnson, A. L.; Price, W. A.; Wong, P. C.; Wexler, R. R.; Timmermans, P.B.M.W.M., Med. Res. Rev., 1992, 12, 149

List continue on next page.

*Primary Examiner*—Bernard Dentz
*Attorney, Agent, or Firm*—Valerie J. Camara; Mark R. Daniel; Joseph F. DiPrima

[57] ABSTRACT

This invention relates to a method for the preparation of a compound of formula I:

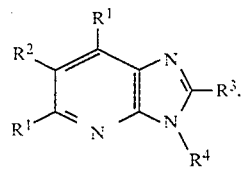

a key intermediate in the synthesis of a series of Angiotensin II receptor antagonists. The invention also relates to a selective reagent for conducting the Hofmann rearrangement, particularly in the formation of a pyridinoimidazolone, which is a precursor to the formation of an imidazopyfidine of formula I. This invention also relates to a method for the preparation of imidazolutidine, a key intermediate in the synthesis of 3-(2'-(N-benzoyl)sulfonamidobiphen-4-yl)-methyl-5,7-dimethyl-2-ethyl-3H-imidazo[4,5-b]pyridine, using pyridinoimidazolone, an unreactive urea.

8 Claims, No Drawings

OTHER PUBLICATIONS

De Laszlo, S. E.; Quagliato, C. S.; Greenlee, W. J.; Patchett, A. A.; Chang, R. S. L.: Lotti, V. J.; Chen, T.-B.; Scheck, S. A.; Faust, K. A.; Kivlighn, S. S.; Schorn, T. S., Zingaro, G. J.; Siegl, P. K. S., J. Med. Chem. 1993, 36, 3207.

Mantlo, N. B.; Chakravarty, P. K.; Ondeyka, D. L.; Siegl, P. K. S.; Chang, R.-S.; Lotti, V. J.: Faust, K. A.; Chen, T.-B.; Schorn, T. W.; Sweet, C. S.; Emmert, S. E; Patchett, A. A.; Greenlee, W. J., J. Med. Chem. 1991, 34, 2922.

Mederski, W. K. R.; Pachler, K. G. R., Tetrahedron, 1992, 48, 10549.

Graboyes, H.; Day, .AR., J. Am. Chem. Soc. 1957, 20, 6421.

Batkowski, T., Rocz. Chem. 1963, 37,385.

Hein, D. W.; Alheim, R. J.; Leavitt, J. J., J. Am. Chem. Soc. 1957, 79, 427.

Barker, J. B.,; Rosenfarb, J.; Caruso, J. A., Angew. Chemie Int. Ed. English 1979, 18, 503.

Dornow, A.; Hahmanu, O., Arch. Pharmaz. Ber. Dtsch. pharmaz, Ges. 1957, 290 20.

Knapp, S.; Albaneze, J.; Schugar, H. J., J. Org. Chem. 1993, 58, 997.

Moriarty, M. R.; Chany II, J. C.; Vaid, R. K.; Prakash, O.; Tuladhar, S. M., J. Org. Chem. 1993, 58, 2482.

PROCESS FOR THE PREPARATION OF IMIDAZOLUTIDINE

BACKGROUND OF THE INVENTION

This invention relates to a method for the preparation of imidazolutidine, a key intermediate in the synthesis of a series of Angiotensin II receptor antagonists. Representative of these antagonists are:

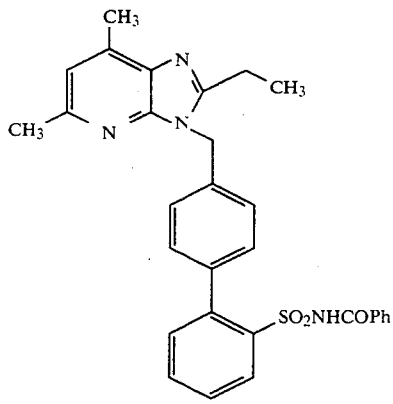

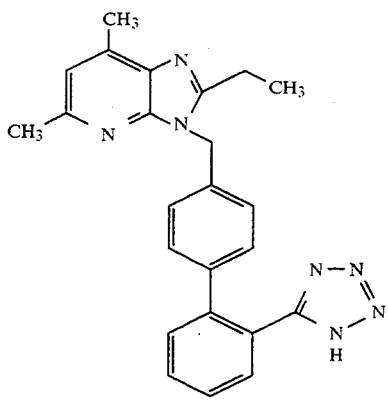

which are disclosed and claimed in U.S. application Ser. No. 516,286 filed May 4, 1990 now U.S. Pat. No. 5,332,744.

The methodology utilized for the synthesis of the imidazopyridine heterocycle relies upon the preparation of a 2,3-diamino precursor using classical chemistry, followed by condensation of the diamine with the appropriate carboxylic acid to form the imidazole. These approaches are often inefficient and lack regiocontrol.

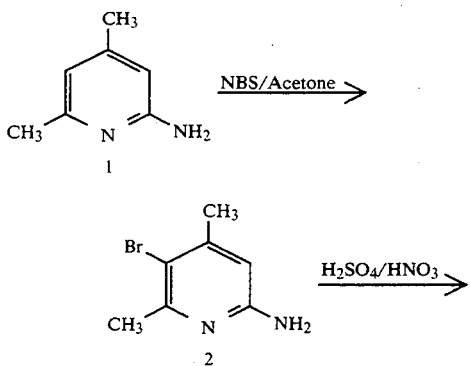

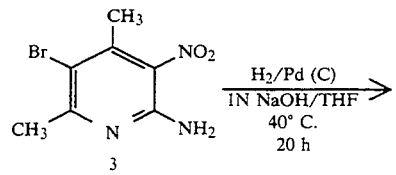

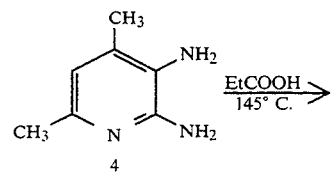

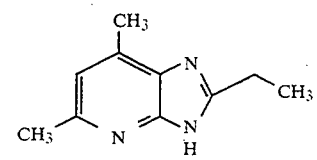

5
[also referred to as Ia]

One of the approaches utilized is described in the above scheme, which is dependent upon obtaining a supply of 2-amino-4,6-lutidine, a starting material, which is available in an impure form. The synthetic route requires a three-step sequence to generate 2,3-diamino-4,6-lutidine, 4. The first of these steps is the bromination of 2-amino-4,6-lutidine with N-bromosuccimide (NBS) added as either a solution in acetone or as a solid to produce 2-amino-5-bromo-4,6-lutidine. Depending upon the addition method used the amounts of the two by-products varied, the 3-bromo analog and the 3,5-dibromo analog. See Table 1 below.

TABLE 1

| Method | 3-Bromo analog | 3,5-Dibromo analog |
| --- | --- | --- |
| solution | 7% | 1% |
| solid | 4.8 % | 8.4% |

The second step is the nitration of the 2-amino-5-bromo-4,6-lutidine to produce the 2-amino-5-bromo-3-nitro-4,6-lutidine. This nitration requires the overnight reaction of the 5-bromo analog with nitric acid and sulfuric acid as a solvent. Over nitration of the 2-amino-5-bromo-4,6-lutidine compound produces a shock-sensitive pyridone compound:

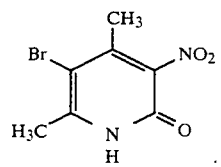

The final step in preparing the diamine is the hydrogenation of the nitro group using palladium on carbon as a catalyst.

The 2,3-diamino-4,6-lutidine is then condensed with propionic acid to form the imidazole ring. This condensation requires large quantities of propionic acid due to the necessity of a constant feed of propionic acid into the reaction.

The process of the instant invention solves the problems associated with using the current methodologies to produce large quantities of the compounds of formula I. The problems include expensive starting materials and use of toxic catalysts and reagents.

SUMMARY OF THE INVENTION

This invention provides a novel method which addresses the drawbacks in the current methodologies used to prepare Angiotensin II antagonists, which feature an imidazo[4,5-b]pyridine. The instant invention provides a methodology for the synthesis of imidazo[4,5-b]pyridines, using a safer and more efficient route. The methodology allows for control of the regioisomers produced. The process is a more cost-effective route using inexpensive and commercially available starting materials. The transformation process using a Lewis acid provides a more rapid route to the preparation of the compounds of formula I. This invention also claims a new reagent for conducting a Hofmann rearrangement.

DETAILED DESCRIPTION OF THE INVENTION

This invention relates to a process for the synthesis of a compound of formula I:

[Structure I]

wherein:
$R^1$ and $R^2$ are independently:
  H,
  $C_{1-6}$ alkyl,
  $C_{1-6}$ alkyl-$C_{3-7}$ cycloalkyl,
  $C_{3-7}$ cycloalkyl,
  aryl, wherein aryl is defined as phenyl or naphthyl, or
  $C_{1-6}$ alkyl-aryl;
$R^3$ is:
  $C_{1-6}$ alkyl,
  $C_{1-6}$ alkyl-$C_{3-7}$ cycloalkyl,
  $C_{3-7}$ cycloalkyl,
  aryl, wherein aryl is defined as phenyl or naphthyl, or
  $C_{1-6}$ alkyl-aryl;
$R^4$ is:
  H,
  $C_{1-6}$ alkyl,
  $C_{1-6}$ alkyl-aryl, wherein aryl is unsubstituted or substituted with X, wherein X is defined as Br, Cl, F, I, or $C_{1-6}$ alkoxy, or
  $C_{1-6}$ alkyl-1,1'-biphenyl, wherein the biphenyl is unsubstituted or substituted with an $R^7$ substituent, wherein $R^7$ is selected from the group consisting of:
    $CO_2H$, $CO_2R^3$, 5-tetrazolyl, $SO_2NHCOR^5$, $SO_2NHCO_2R^5$;
$R^5$ is:
  $C_{1-6}$ alkyl,
  aryl, wherein aryl is defined as phenyl or naphthyl, or
  $C_{1-6}$ alkyl-aryl;

which comprises
  (a) condensing

[Structure: H₂N-C(O)-CH₂-C(NH·HCl)=... NHR⁴], with [Structure: R¹-C(O)-CHR²-C(O)-R¹]

in a basic solution at a temperature range of about 25° C. (room temperature) to about 70° C. to produce a substituted pyridine

[Structure: substituted pyridine with R¹, R², NH₂, NHR⁴]

(b) reacting the substituted pyridine with

[Structure: R⁶O-C(O)-(CH₂)ₙ-C(O)-NM(Br)]

wherein:
  $R^6$ is defined as M, H or $C_{1-6}$ alkyl;
  M is defined a $K^+$, $Na^+$, $Li^+$, $Cs^+$, or $Ba^{+2}$;
  n is 2 to 5: in an aqueous basic solution to produce a cyclic urea:

[Structure: cyclic urea]

(c) heating the cyclic urea at a temperature range of between about 110° C. to about 180° C. in a solvent of $R^3CO_2H$ and $(R^3CO)_2O$ and a Lewis acid to produce the compound of formula I.

An embodiment of this invention relates to a process for the synthesis of a compound of formula I:

[Structure I]

which comprises
  (a) condensing

[Structure: H₂N-C(O)-CH₂-C(NH·HCl)=NHR⁴],

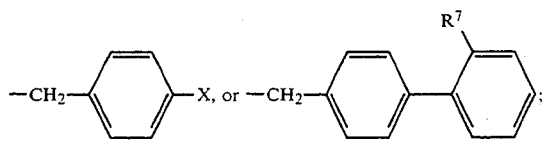

with

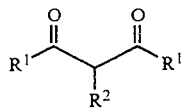

in a basic solution at a temperature range of about 25° C. (room temperature) to about 70° C. to produce a substituted pyridine

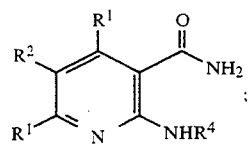

(b) reacting the substituted pyridine with

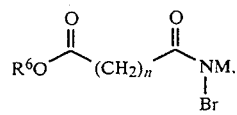

wherein:
$R^6$ is defined as M, H or $C_{1-6}$ alkyl;
M is defined a $K^+$, $Na^+$, $Li^+$, $Cs^+$ or $Ba^{+2}$;
n is 2 to 5; in an aqueous basic solution to produce a cyclic urea:

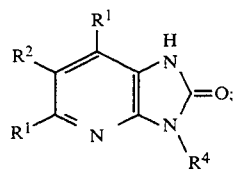

(c) heating the cyclic urea at a temperature range of between about 110° C. to about 180° C. in a solvent of $R^3CO_2H$ and $(R^3CO)_2O$ and a Lewis acid to produce the compound of formula I.

A second embodiment of this invention relates to a process for the synthesis of a compound of formula Ia:

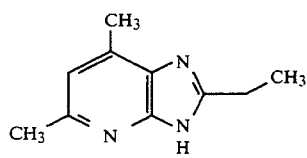

which comprises
(a) condensing

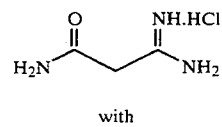

with

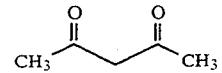

in a basic solution at a temperature range of about 25° C. (room temperature) to about 70° C. to produce a substituted pyridine

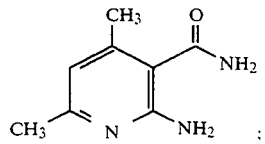

(b) reacting the substituted pyridine with

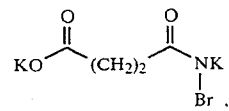

in an aqueous basic solution to produce a cyclic urea:

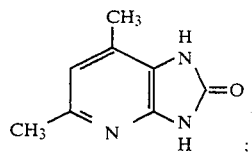

(c) heating the cyclic urea at a temperature range of between about 110° C. to about 180° C. in a solvent of $CH_3CH_2CO_2H$ and $(CH_3CH_2CO)_2O$ and $MgCl_2$ to produce the compound of formula Ia.

An embodiment of the invention is the process for the preparation of an imidazopyridine of formula I:

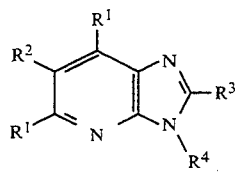

wherein:
$R^1$ and $R^2$ are independently:
H,
$C_{1-6}$ alkyl,
$C_{1-6}$ alkyl-$C_{3-7}$ cycloalkyl,
$C_{3-7}$ cycloalkyl,
aryl, wherein aryl is defined as phenyl or naphthyl, or
$C_{1-6}$ alkyl-aryl;
$R^3$ is:
$C_{1-6}$ alkyl,
$C_{1-6}$ alkyl-$C_{3-7}$ cycloalkyl,
$C_{3-7}$ cycloalkyl, aryl, wherein aryl is defined as phenyl or naphthyl, or C$_{1-6}$ alkyl-aryl;

R$^4$ is:

H,

C$_{1-6}$ alkyl,

C$_{1-6}$ alkyl-aryl, wherein aryl is unsubstituted or substituted with X, wherein X is defined as Br, Cl, F, I, or C$_{1-6}$ alkoxy, or C$_{1-6}$ alkyl-1,1'-biphenyl, wherein the biphenyl is unsubstituted or substituted with an R$^7$ substituent, wherein R$^7$ is selected from the group consisting of: CO$_2$H, CO$_2$R$^3$, 5-tetrazolyl, SO$_2$NHCOR$^5$, SO$_2$NHCO$_2$R$^5$;

R$^5$ is:

C$_{1-6}$ alkyl, aryl, wherein aryl is defined as phenyl or naphthyl, or

C$_{1-6}$ alkyl-aryl;

comprising heating a cyclic urea

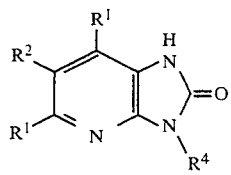

at a temperature range of between about 110° C. to about 180° C. in a solvent consisting essentially of R$^3$CO$_2$H and (R$^3$CO)$_2$O and a Lewis acid.

A embodiment of the invention is a process for the preparation of a compound of formula II

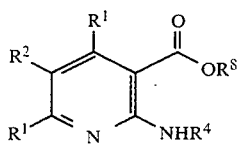

wherein:

R$^1$ and R$^2$ are independently:

H,

C$_{1-6}$ alkyl,

C$_{1-6}$ alkyl-C$_{3-7}$ cycloalkyl,

C$_{3-7}$ cycloalkyl, aryl, wherein aryl is defined as phenyl or naphthyl, or

C$_{1-6}$ alkyl-aryl;

R$^3$ is:

C$_{1-6}$ alkyl,

C$_{1-6}$ alkyl-C$_{3-7}$ cycloalkyl,

C$_{3-7}$ cycloalkyl, aryl, wherein aryl is defined as phenyl or naphthyl, or

C$_{1-6}$ alkyl-aryl;

R$^4$ is:

H,

C$_{1-6}$ alkyl,

C$_{1-6}$ alkyl-aryl, wherein aryl is unsubstituted or substituted with X, wherein X is defined as Br, Cl, F, I, or C$_{1-6}$ alkoxy, or C$_{1-6}$ alkyl-1,1'-biphenyl, wherein the biphenyl is unsubstituted or substituted with an R$^7$ substituent, wherein R$^7$ is selected from the group consisting of: CO$_2$H, CO$_2$R$^3$, tetrazol-5-yl, SO$_2$NHCOR$^5$, SO$_2$NHCO$_2$R$^5$;

R$^5$ is:

C$_{1-6}$ alkyl, aryl, wherein aryl is defined as phenyl or naphthyl, or

C$_{1-6}$ alkyl-aryl; and

R$^8$ is C$_{1-6}$ alkyl;

which comprises the steps of: reacting

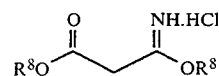

with R$^4$NH$_2$ in an C$_{1-6}$ alkanol solution from about 20° C. to about 80° C. to produce a secondary amine

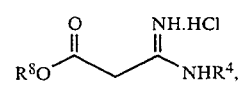

cooling the reaction mixture to between about 20° C. and about 25° C. (room temperature),

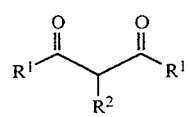

in a basic solution at a temperature range of about 20° C. to about 25° C. (room temperature) to produce the substituted pyridine of formula II.

Another embodiment of the invention is the process for the preparation of a compound of formula IIa:

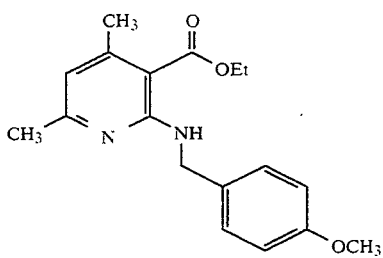

which comprises the steps of: reacting

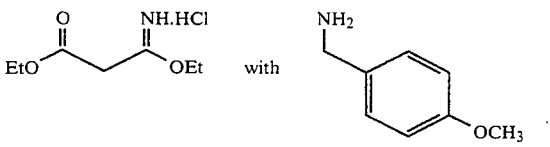

in an ethanol solution from about 20° C. to about 80° C. to produce a secondary amine

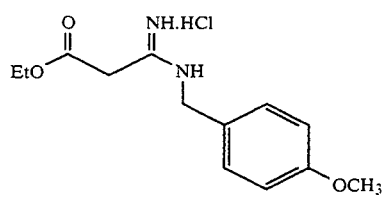

cooling the reaction mixture to between about 20° C. and about 25° C. (room temperature),

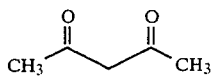

in a basic solution at a temperature range of about 20° C. to about 25° C. (room temperature) to produce the substituted pyridine of formula IIa.

The schemes outlined below provide a description of the steps utilized to prepare the imidazo[4,5-b]pyridine of formula I.

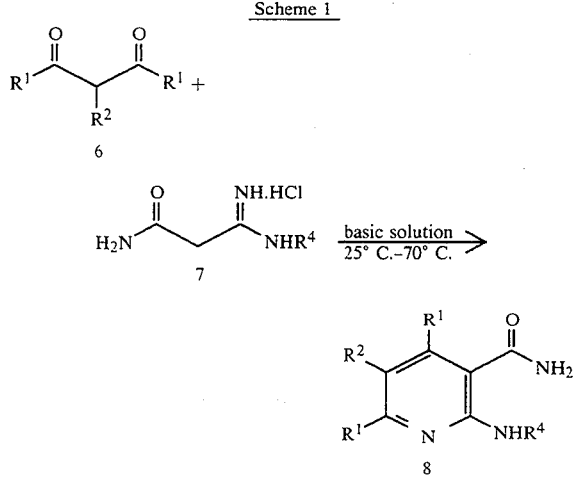

A reaction between a 1,3-dione 6 and a malonic acid derivative 7 under basic conditions at a temperature range of between about 25° C. (room temperature) to about 70° C. produces a condensation product, pyridine 8, as described in Scheme 1. The basic solutions are combinations of an alkanol and a Group Ia or Group IIa hydroxide. The alcohols which are useful in conducting this reaction are: methanol and ethanol. The bases which are useful in conducting this reaction are: CsOH, KOH, NaOH, LiOH and Ba(OH)$_2$.

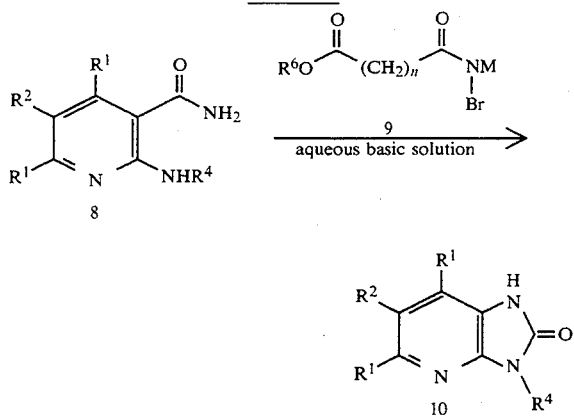

The reaction of the pyridine 8 with N-bromoacid-amide derivative 9 trader aqueous, basic conditions at a temperature range of between about −20° C. to about 0° C. results in the Holmann rearrangement product, pyridinoimidazolone 10. The basic solutions which are useful are combinations of an alkanol and a Group Ia or Group IIa hydroxide. The alcohols which are useful in conducting this reaction are: methanol and ethanol. The specific bases which are useful in conducting this reaction are: KOH, NaOH, LiOH, CsOH and Ba(OH)$_2$. The preferred alcohol is methanol and the preferred base is potassium hydroxide. The preferred reaction temperature is between about −5° C. to about 0° C.

An alternative set of reaction conditions is where the N-bromoacid-amide derivative 9 reagent is replaced with iodobenzene diacetate in a basic alcoholic solution at a temperature range of about −5° C. to about 25° C. (room temperature).

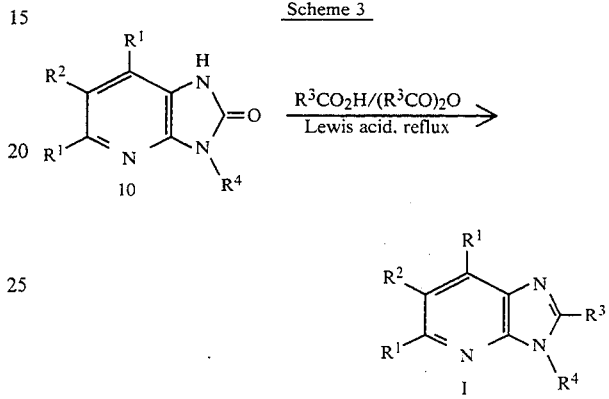

The reaction of pyridinoimidazolone 10 with a carboxylic acid, an acid anhydride and a Lewis acid under refluxing temperatures produces the imidazopyfidine of Formula I. The Lewis acids useful in carrying out this transformation are MgX$_2$; ZnX$_2$; CaX$_2$; LiX; CsX; wherein X is defined as bromo, chloro, iodo, or fluoro; MgSO$_4$; ZnSO$_4$; CaSO$_4$; Li$_2$SO$_4$; Cs$_2$SO$_4$; Mg(O$_3$SCF$_3$)$_2$; Zn(O$_3$SCF$_3$)$_2$; Ca(O$_3$SCF$_3$)$_2$; LiO$_3$SCF$_3$; or CsO$_3$SCF$_3$. The preferred Lewis acid for catalyzing this transformation is MgCl$_2$ or MgSO$_4$.

An embodiment of this invention is the identification of the reagent:

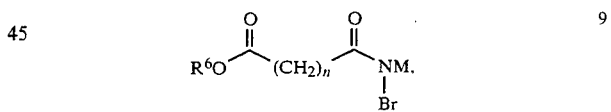

responsible for the Hofmann rearrangement described in Scheme 2 above. The preferred reagent for this reaction is N-bromosuccinamic acid potassium salt. This reagent is formed by reacting N-bromosuccinimide at low temperatures, about −5° C., under aqueous basic conditions for between 5 minutes and 9 days. The preferrable reaction time is about 16 hours using aqueous potassium hydroxide.

An NMR study of the fate of NBS in the basic solution was conducted. The solution was prepared as usual before addition to the nicotinamide: KOH was dissolved in D$_2$O and the resulting solution was cooled to about −5° C. to about 0° C. NBS was then added and the mixture was stirred at this temperature until the NBS dissolved. The $^1$H and $^{13}$C NMR of the resulting yellow solution were taken over time at −5° C. At T=5 minutes essentially no NBS remained; two species, one major (85%) and one minor (15%), were generated immediately upon the addition of the NBS to the basic D₂O. The minor compound showed a singlet at 2.30 ppm in the ¹H NMR and one aliphatic carbon and one carbonyl carbon by ¹³C NMR. This corresponded to a symmetric compound which was determined to be the potassium salt of succinimide 12 (Scheme 4).

The major compound at T=5 minutes showed a splitting pattern characteristic of an unsymmetric molecule. The ¹³C NMR which showed two distinct carbonyl resonances and two distinct aliphatic resonances suggested this as well. This unsymmetric derivative of NBS is the active oxidizing species and not NBS. Over time NBS (11), in equilibrium with the succinimide salt 12, is convened to this oxidizing species 9a, an irreversible reaction (Scheme 4). At T=5 minutes there were only 85% of 9a and 15% of 12. After 5.5 hours, 9a had grown to 95.5% with only 4.5% of 12 remaining. After aging for 16 hours at −5° C., the oxidizing agent 9a had grown to 96.2% and the succinimide salt had decreased to 2.3%. Previously unobserved, 1.5% of a new species 14 had been generated. The β-alanine derivative 14 is a rearrangement product of the N-bromo species 9a; the reagent itself can undergo Hofmann rearrangement to yield the carbamate. This explains the degradation of NBS in solution overtime.

TABLE 1

Effect of Age Time At −5° C. On Generation Brominating Species

| Age Time | % 12 | % 9a | % 13 | % 14 |
|---|---|---|---|---|
| 5 minutes | 15 | 85 | — | — |
| 5.5 hours | 4.5 | 95.5 | — | — |
| 16 hours | 2.3 | 96.2 | — | 1.5 |
| 9 days | 0.5 | 78 | 16.5 | 5 |

The true oxidizing agent in the Hofmann rearrangement is N-bromosuccinamic acid 9a. Support for this structure was also established by conducting the desired Hofmann rearrangement on nicotinamide 8. The NMR of the filtrate after the product 10 was filtered showed one major compound with two carbonyl and two aliphatic resonances, which corresponds with the ¹H and ¹³C NMR for succinamic acid in a spiking experiment. Isolation of succinamic acid from the filtrate is additional collaborating evidence for N-bromosuccinamic acid acting as the oxidizing species. Attempts to independently synthesize N-bromosuccinamic acid by addition of KOH/Br₂ to succinamic acid failed. The N-bromosuccinamic acid 9a is derived only from ring opening of NBS and cannot be prepared by the reaction of succinamic acid with KOBr.

Scheme 4

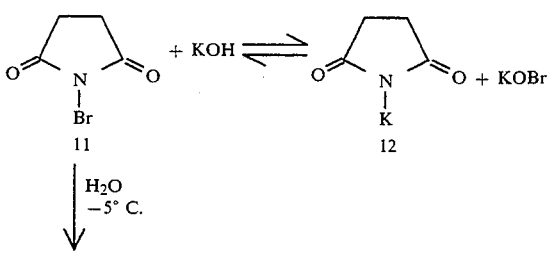

-continued
Scheme 4

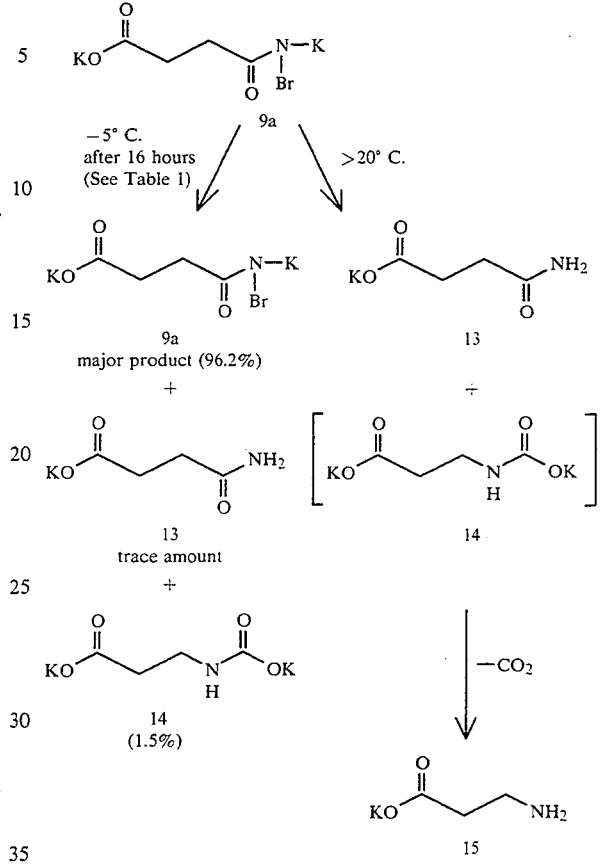

NMR studies of the NBS-KOH reagent mixture were also conducted in a D₂O/CD₃OD medium (3:7) at −5° C. The major compound is indeed the same unsymmetric compound generated in D₂O alone. The succinimide salt 12 was also observed as well as another unsymmetric compound which appeared to be the methyl ester of N-bromosuccinamic acid 16 (Scheme 5). This species disappeared with time from hydrolysis in the basic medium to yield N-bromosuccinamic acid 9a. By using only one equivalent of KOH, thereby suppressing the saponification, the ester was the major compound observed. Species 16 may also act as an oxidizing agent in H₂O/MeOH.

Stability studies of the reagent in both media were also carried out with NMR. In D₂O at −5° C. 9a remained fairly stable; even after 9 days, 78% remained. Some decomposition to potassium succinamate 13 and rearrangement to the carbamate 14 was observed. After an aged solution was allowed to warm to room temperature, approximately half of the solution had decomposed to 13 within 30 minutes. Over 2 hours virtually all of 9a had decomposed to 13(70%) and to four Hofmann rearrangement products: 14, 15 and two unidentified species (30%). The reagent is also stable in D₂O/CD₃OD at −5° C. After 8 days at −5° C., 62% of 9a remained. While aging at room temperature, the oxidizing agent rapidly rearranged to the isocyanate which was quenched by MeOH to yield 67% of the corresponding methyl carbamate 17. The remaining 33% of the original reagent decomposed to 13.

These findings were extremely crucial to understanding why the reaction had failed to go to completion.

Previously, the KOH/NBS solution had been added to the substrate after only a 5-min age; only 85% of the desired reagent is generated in this time frame (Table 1). Therefore, it is necessary to age the KOH/NBS solution further at −5° C. in order to convert the succinimide salt 12 completely to the oxidizing species 9a (Scheme 4). A 16 h age provided 96% of 9a by NMR assay. Addition of this mixture to the nicotinamide at −20° C. increased the conversion of the amide 8 to the urea 10 from 75–80% to 90–95% by W % assay.

This rapid decomposition of the NBS-KOH mixture at room temperature also explains why previously the Hofmann reaction did not complete. As the reagent was syringed into the reaction flask, decomposition had already occurred. The instability of the reagent at room temperature was demonstrated; the NBS-KOH mixture was aged at −5° C. for 16 hours and then at room temperature for 2 hours. This reagent mixture only gave a 17 W %-yield of the urea with 82.5 W % of the nicotinamide recovered. This is consistent with the decomposition observed by NMR at room temperature. It is crucial to maintain the reagent at −5° C. during the addition.

Scheme 5

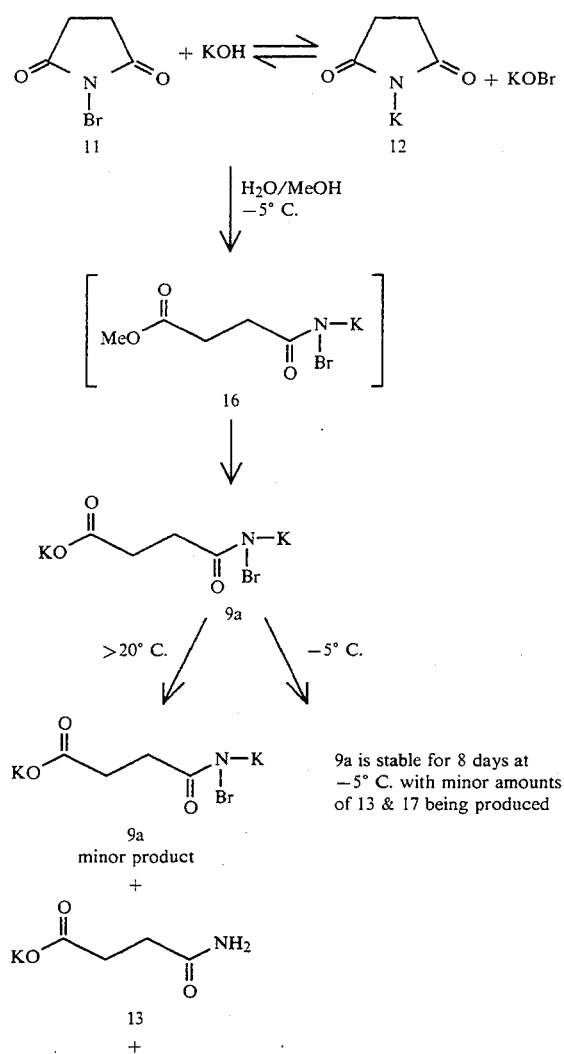

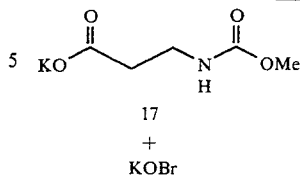

+ KOBr

An NMR study of the reaction was carried out in order to elucidate the mechanism of the Hofmann rearrangement. This was initially attempted on the aminonicotinamide 8, however the precipitation of the urea 10 made it difficult to observe anything by NMR. The current understanding of the reaction is that the oxidizing agent transfers the bromine to the nicotinamide; the N-bromoamide rearranges to the isocyanate which is then captured by the amino group intramolecularly to yield the cyclic urea.

The use of the new reagent for carrying out the Hofmann rearrangement was demonstrated on a 3 g scale using 1 equivalent of the reagent. The product was isolated by filtration and washed with water to remove inorganic salts. The isolated yield of 10 was 2.39 g (81%) with a purity of >99% (HPLC wt % assay). The amount of product in the mother liquors was 321 mg (11 W %). The mother liquors also contained 274 mg of the nicotinamide (9 W %). The incomplete formation of the oxidizing agent prevents the complete reaction with one equivalent; even after aging for 16 hours only 96% of 9a is generated. Excess reagent further increased the conversion to the urea: 1.1 equivalents of the NBS gave 96 W % conversion to the urea with only 1.8% of nicotinamide remaining.

The following examples further illustrate the method for preparing compounds of Formula I and as such, are not to be considered or construed as limiting the invention recited in the appended claims.

EXAMPLE I

Process for the preparation of 4,6-dimethylpyridoimidazolone 10a using Iodobenzene Diacetate—Method A

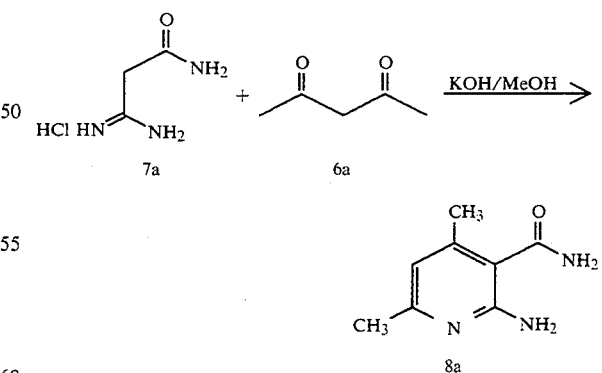

Step A

Preparation of 2-amino-4,6-dimethylnicotinamide 8a

In a 12-L three-necked flask containing methanol (5.15 L) fitted with an overhead stirrer is added potassium hydroxide (98.14 g, 1.75 mol) as a solid at 23° C. under a nitrogen atmosphere. The temperature rises to 30° C. over 5 minutes. The mixture is allowed to cool to room temperature before the addition of 7a. Malonamidamidine hydrochloride (200 g, 1.45 mol) is added as a solid to the basic solution at 23° C. over 10 minutes under a nitrogen atmosphere. The addition is endothermic; the temperature decreases to 19° C. over 10 minutes. Neat 2,4-pentanedione (149.3 mL, 1.45 mol) is added to the milky-white suspension dropwise over 15 minutes at room temperature. The addition is slightly exothermic: controlled addition over 15 minutes only gives a 2° C. exotherm. The reaction mixture is aged at room temperature for 24 hours. During the age the nicotinamide precipitates out of the reaction as does KCl.

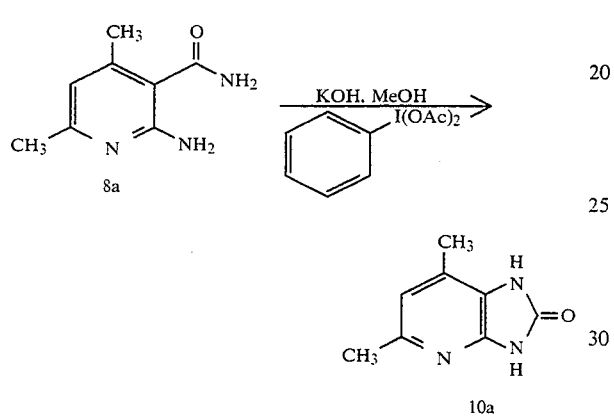

Step B

Preparation of 4,6-dimethylpyridoimidazolone 10a

Methanol (3.35 L) is added to the reaction mixture of Step A. In a separate 5-L three-necked flask, potassium hydroxide (203.5 g, 3.63 mol) is dissolved in methanol (1 L). The solution is allowed to cool to room temperature and is then added to the amide mixture at room temperature over 15 minutes. This mixture is allowed to stir for 30 minutes and is then cooled to −5° C. Iodobenzene diacetate (491.7 g, 1.45 mol) is added as a solid over 30 minutes. The addition of iodobenzene diacetate is exothermic; cooling with dry ice-isopropanol keeps the reaction temperature below −5° C. The resulting mixture is warmed to room temperature over 3 hours and is aged at room temperature for 12 hours. The product 10a precipitates out of the reaction mixture during the age. The reaction mixture is filtered and the filter cake is washed with methanol (7.5 L) and vacuum dried to afford 254.67 g of 10a as a white solid in 78.6% yield. The purity is 73.6 W % by HPLC as compared to a recrystallized sample of 10a and the A % purity is 99%. The assay purity of the isolated product is 73.6% due to contamination with salts. Titration of the crude sample reveals that KCl and KOH account for 26.4% of the weight of the crude product. The amount of product in the mother liquors is 27.54 g (11.5%) by assay. The mother liquor also contains the intermediate amino nicotinamide (4.5% by HPLC A %) and the impurity, 18 (5.4% by HPLC A %) characterized as:

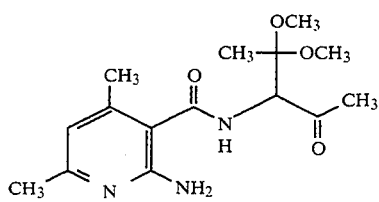

EXAMPLE 2

Process for the preparation of 4,6-dimethyl-pyridoimidazolone 10a using N-Bromosuccinamic Acid dipotassium—Method B

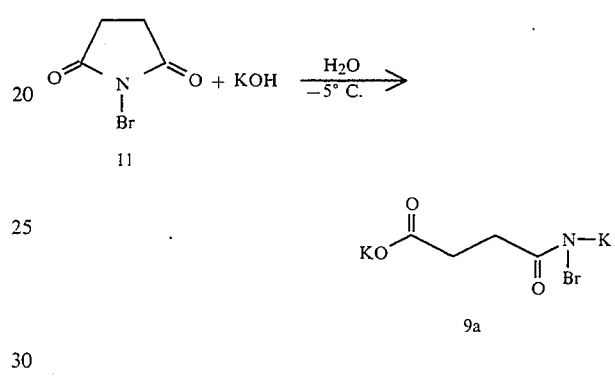

Step A

Preparation of N-Bromosuccinamic Acid dipotassium 9a

To a 50-mL three-necked flask containing water (18 mL) equipped with a magnetic stirrer is added potassium hydroxide (2.53 g, 0.045 mol) as a solid at 23° C. under a nitrogen atmosphere. The solution is stirred for 10 minutes to allow the KOH to dissolve completely. The temperature rises to 30° C. over the age. The mixture is cooled to 0° C. and N-bromosuccinimide (11) (3.22 g, 0.018 mol) is added as a solid over 5 minutes under a nitrogen atmosphere. The mixture is stirred at 0° C. until all the solid is dissolved giving a clear-yellow solution. The solution is aged at −5° C. in a glycol-water bath for 16 hours. After 16 hours the optimum conversion to the brominating species is observed (96%). Aging further causes some rearrangement of 9a to the β-alanine derivative.

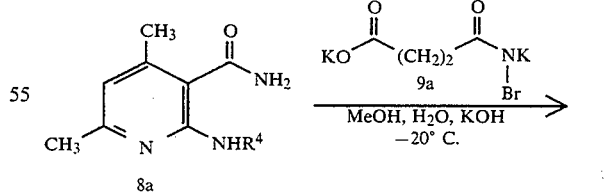

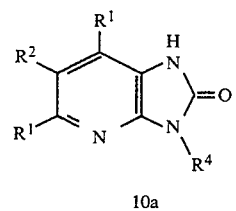

Step B

Preparation of 4,6-dimethylpyridoimidazolone 10 using N-Bromosuccinamic Acid dipotassium In a 250-mL three-necked flask containing methanol (42 mL) fitted with an overhead stirrer is added 2-amino-4,6-dimethylnicotinamide (8a) (3.0 g, 0.018 mol) as a solid at 23° C. under a nitrogen atmosphere. The resulting mixture is stirred at room temperature under a nitrogen atmosphere for five minutes to dissolve 8a completely. The solution is cooled to −20° C. before the addition of 9a. To the clear, colorless solution of 8a at −20° C. is added the solution of 9 [prepared from 0.018 mol of N-bromosuccinimide and 0.045 mol of potassium hydroxide in water (18 mL)] via a double-tipped needle under a nitrogen atmosphere. The solution of 9a must be maintained at −5° C. during the addition in order to prevent decomposition to 13 and rearrangement to 15. The resulting mixture is aged at −20° C. for 5 hours. The product 10a precipitates out of the reaction mixture during the age. The reaction mixture is filtered and the filter cake is washed with water (10 mL) and vacuum dried to afford 2.39 g of 10a as a white solid in 81% yield. The purity is 99 W % by HPLC as compared to a recrystallized sample of 10a and the A % purity is 99%. The amount of product in the mother liquors is 321 mg(11%) by assay. The mother liquor also contains 274 mg of 8a (9%) by assay.

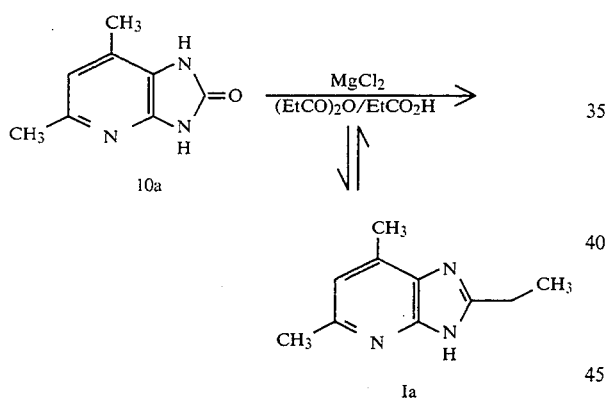

Step C

Preparation of Imidazolutidine I

To the crude 4,6-dimethylpyridoimidazolone 10a (247 g, 1.5 mol) in a 12-L three-necked flask equipped with an overhead stirrer and a reflux condenser is added propionic acid (2.146 L, 28.77 mol) followed by propionic anhydride (2.146 L, 16.74 mol). The resulting mixture is stirred at room temperature under a nitrogen atmosphere for 5 minutes. To the milky-white suspension is added solid magnesium chloride (143.4 g, 1.5 mol) at room temperature and the mixture is heated to reflux. The reaction mixture is refluxed for 7–8 hours at 145° C. The reaction time is determined by HPLC. The reaction mixture is cooled to 60° C. and methanol is added (2.5 L). The resulting mixture is aged at 64° C. in order to cleave the N-propionyl imidazolutidine to imidazolutidine, as well as to hydrolyze the propionic anhydride to methyl propionate. The reaction mixture is concentrated by distillation in vacuo, removing methanol, propionic acid, and methyl propionate. Water (550 mL) is added to the reaction mixture and the final reaction volume is adjusted to 300 mL. The solution is cooled to 40° C. and the pH is adjusted to 8.7 by addition of concentrated ammonium hydroxide (175 mL) maintaining the temperature below 50° C. The resulting slurry is cooled to −5° C. and is aged at that temperature for 1.5 hours. The slurry is filtered and the cake is washed with cold water (0° C., 3.3 L), until all the ammonium propionate is removed. The cake is dried in a vacuum oven at 50° C. with a nitrogen purge for 48 hours. The isolated yield of imidazolutidine Ia is 165.5 g (81% yield) with a W % purity of 94% and an A % purity of >99%. Measurement of the KF and TG shows 0.7% of water is present in the isolated compound and measurement of chloride shows 4% by weight of chloride salts composed of either KCl or MgCl$_2$. Recrystallization of the crude imidazolutidine from water increases the W % purity to 98%.

The intermediates of this reaction were characterized as:

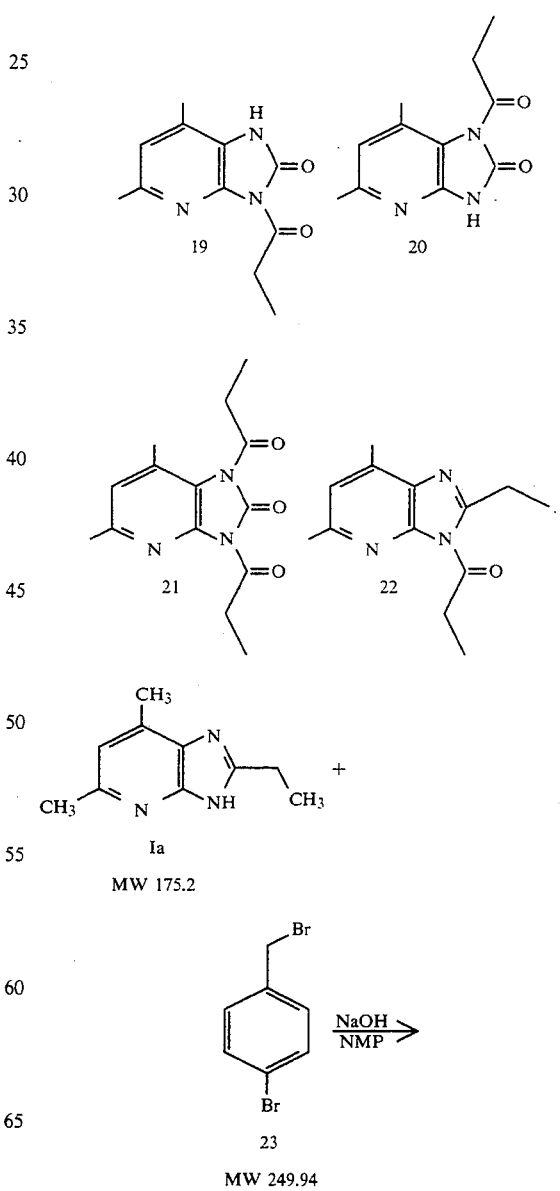

EXAMPLE 3

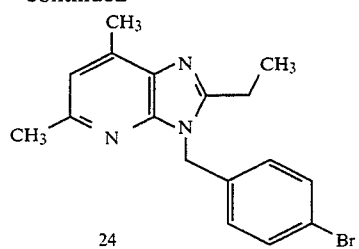

24

+

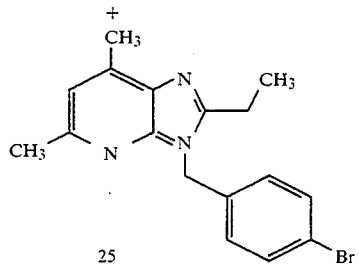

25

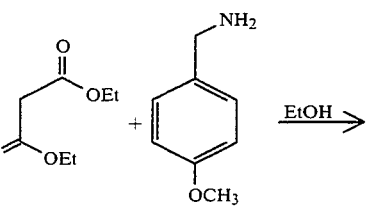

Step D

Preparation of Benzylated Imidazolutidine 24

To a 250-mL three-necked flask fitted with an overhead stirrer is added imidazolutidine Ia (5.30 g, 0.028 mol) as a solid at 23° C. followed by addition of N-methylpyrrolidine (20 mL) under a nitrogen atmosphere. The mixture is stirred for 5 minutes until the imidazolutidine is completely dissolved. In a separate 25-mL flask, freshly ground sodium hydroxide (2.35 g, 0.057 mol) is dissolved in N-methylpyrrolidine (5 mL). The temperature rises to 30° C. The mixture is allowed to cool to room temperature before addition to the reaction mixture. The sodium hydroxide solution is added to the solution of Ia at room temperature over 5 minutes. The addition of the NaOH solution is exothermic. Controlled addition only leads to a 2° C. exotherm. The solution is aged at room temperature under nitrogen atmosphere for 1 hour. The reaction mixture is cooled to 0° C. and a solution of 4-bromobenzyl bromide (23) (7.42 g, 0.029 mol) in N-methylpyrrolidine (5 mL) is added dropwise over 5 min to the reaction mixture. The addition of 23 is slightly exothermic. With controlled addition from an addition funnel, the temperature can be maintained at 0° C. The reaction mixture is warmed to room temperature directly after the addition and aged for 2 hours. The reaction mixture is cooled to 0° C. and water (90 mL) is added dropwise from an addition funnel over 15 minutes. Once the addition is complete, the reaction mixture is allowed to warm to room temperature and is aged for 1 h. The solid is filtered and washed with N-methylpyrrollidine/water (1:3, 20 mL) and water (2×50 mL) to afford 8.08 g of 24 as a tan solid in 79.3% yield. The purity is 96.3 W % by HPLC as compared to a recrystallized sample of 24. The mother liquors contained 235 mg of 24. The ratio of regioisomers 24:25 was determined by NMR to be 87:13.

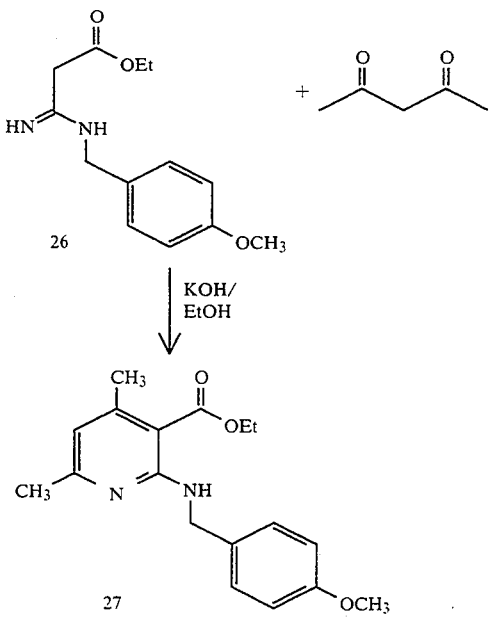

Process for the preparation of 2-(4-methoxybenzylamino)-4,6-dimethylnicotinamide 27.

In a three-necked flask containing ethanol (6.12mL) is added ethyl 3-amino-3-ethoxyacrylate hydrochloride(3g, 15.3mmol). The solution is treated with 4-methoxybenzylamine(2mL, 15.3mmol) and the mixture is stirred at 22° C. for 1.5 h. The reaction mixture was heated to 80° C. for 3 h. The reaction is cooled to 22° C. and an ethanolic solution of potassium hydroxide (0.86 g, 15.3 mmol, 25.0 mL of ethanol) is added. Neat 2,4-pentanedione (1.57 mL, 15.3 mmol) is added to the solution dropwise over 15 minutes at room temperature. The reaction mixture is aged at room temperature for 24 hours. During the age the nicotinate precipitates out of the reaction as does KCl. The reaction mixture is concentrated in vacuo. The crude mixture is chromatographed on silica gel to afford a 70% yield of the product, ethyl 2-(4-methoxybenzylamino )-4,6-dimethylnicotinate, 27.

$^1$H NMR(300.1 MHz-DMSO-d$_6$) δ1.2(t, 2H), 2.27(s, 3H), 2.33(s, 3H), 3.71(s, 3H), 4.2(q, 2H), 4.55(d, 2H), 6.29(s, 1H), 6.87(d, 2H), 7.26(d, 2H), 7.94(t, 1H)

$^{13}$C NMR(75.4 MHz-DMSO-d$_6$) δ13.84, 22.54, 24.08, 43.73, 54.79, 60.35, 113.54, 114.55, 128.70, 131.97, 150.23,157.56, 158.12, 159.85.

EXAMPLE 4

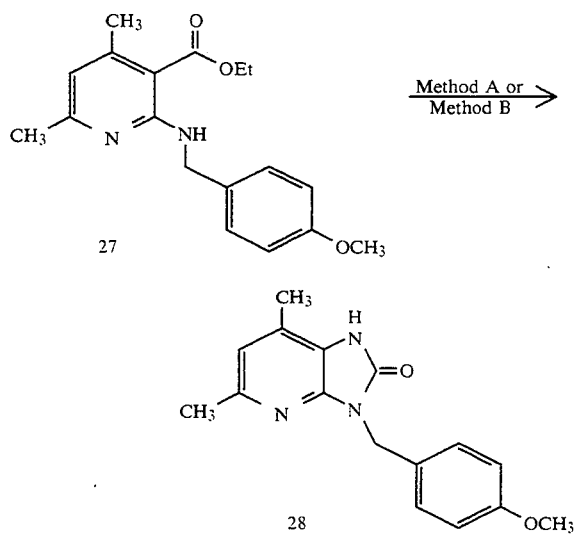

Process for the preparation of 2-(4-methoxybenzylamino)-4,6-dimethylpyridoimidazolone, 28.

Method A

The titled compound is prepared following the procedure described in Kuo, G.; Bacon, E. D.; Singh, B.; Eissenstat, M. A.; Lesher, G. Y. *J. Heterocyclic Chem.*, 1993, 30, 37, using the product of Example 3.

Method B

The titled compound is prepared by first reacting the product of Example 3 with ammonia in ethanol or methanol to form the amide and then following the procedure described in Example 2, Step B.

EXAMPLE 5

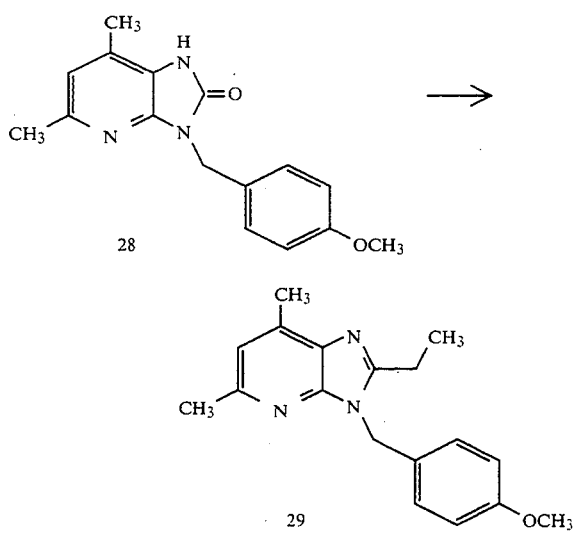

Process for the preparation of 2-(4-methoxybenzylamino)-imidazolutidine, 29.

The titled compound is prepared from 2-(4-methoxybenzylamino) -4,6-dimethylpyridoimidazolone using the procedure described in Example 2, Step C.

EXAMPLES 6–11

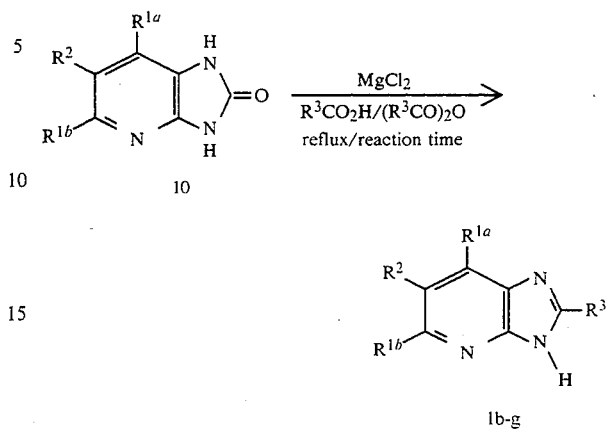

Following the procedure described in Example 2, Step C the pyridoimidazolone 10 was reacted with $R^3CO_2H/(R^3CO)_2O$ at the stated temperature for the stated reaction time to form the imidazo[4,5-b]pyridine Ia-f in the isolated yield as set forth in the Table below:

| Str/Ex | $R^{1a}$ | $R^2$ | $R^{1b}$ | $R^3$ | Temperature (°C.) | Reaction time (h) | Isolated yield (%) |
|---|---|---|---|---|---|---|---|
| Ib/6 | H | H | H | Bu | 150 | 8 | 78 |
| Ic/7 | Me | H | Me | Et | 145 | 7 | 85 |
| Id/8 | Me | H | Me | Me | 116 | 48 | 80 |
| Ie/9 | Me | H | Me | Bu | 150 | 9 | 90 |
| If/10 | H | Et | Me | Pr | 150 | 8 | 75 |
| Ig/11 | Me | Me | Me | Ph | 150 | 10 | 70 |

EXAMPLE 6

The spectral data for imidazo[4,5-b]pyridine Ib was as follows:
$^1$H NMR(300.1 MHz-DMSO-$d_6$/CF$_3$COOH) δ0.95(t, 3H), 1.45(m, 2H), 1.9(m, 2H), 3.05(t, 2H), 7.25(d,d, 1H), 8.05(d, 1H), 8.3(d, 1H).

EXAMPLE 7

The spectral data for imidazo[4,5-b]pyridine Ic were as follows:
$^1$H NMR(300.1 MHz-DMSO-$d_6$/CF$_3$COOH) δ1.35(t, 3H), 2.53(s, 3H), 2.57(s, 3H), 2.92(q, 2H), 6.78(s, 1H)
$^{13}$C NMR(75.4 MHz-DMSO-$d_6$/CF$_3$COOH) δ12.98, 16.57, 23.73, 118.75, 132.91, 137.92, 148.97, 150.88, 156.73.

EXAMPLE 8

The spectral data for imidazo[4,5-b]pyridine Id were as follows:
$^1$H NMR(300.1 MHz-DMSO-$d_6$/CF$_3$COOH) 15 2.43(s, 3H), 2.44(s, 3H), 2.47(s, 3H), 6.82(s, 1H)
$^{13}$C NMR(75.4 MHz-DMSO-$d_6$/CF$_3$COOH) δ14.42, 16.1, 22.81, 118.59, 128.5, 135.17, 148.5, 150.6, 152.8.

EXAMPLE 9

The spectral data for imidazo[4,5-b]pyridine Ie were as follows:
$^1$H NMR(300.1 MHz-DMSO-$d_6$/CF$_3$COOH) δ0.9(t, 3H), 1.35(m, 2H), 1.73(m, 2H), 2.44(s, 3H), 2.45(s, 3H), 2.7(t, 2H), 6.82(s, 1H).

$^{13}$C NMR(75.4 MHz-DMSO-d$_6$/CF$_3$COOH) 15 13.5, 16.21, 21.6, 23.28, 28.31, 29.45, 117.95, 128.9, 134.69, 149.63, 150.47, 155.86.

EXAMPLE 10

The spectral data for imidazo[4,5-b]pyridine If were as follows:

$^1$H NMR(300.1 MHz-DMSO-d6 ) δ0.95(t, 3H), 1.2(t, 3H) 1.75(m, 2H), 2.5(s, 3H), 2.7(q, 2H), 2.8(t, 3H), 7.55–7.65(bs, 1H).

$^{13}$C NMR(75.4 MHz-DMSO-d6 ) δ14.8, 18.5, 21.2, 22.5, 25.4, 30.5, 124.8, 130.6, 133.9, 149.3, 155.5.

EXAMPLE 11

The spectral data for imidazo[4,5-b]pyridine Ig were as follows:

$^1$H NMR(300.1 MHz-DMSO-d$_6$/CF$_3$COOH) 15 2.32(s, 3H), 2.67(s, 3H), 2.71 (s, 3H), 7.64(m, 3H), 8.29(m, 2H).

$^{13}$C NMR(75.4 MHz-DMSO-d$_6$/CF$_3$COOH) δ14.0, 15.4, 19.0, 126.5, 127.6, 127.8, 129.3, 129.7, 132.0, 139.8, 142.4, 145.7, 155.8.

What is claimed is:

1. A process for the preparation of a compound of formula I:

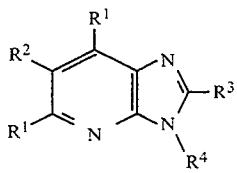

wherein:

R$^1$ and R$^2$ are independently:
H,
C$_{1-6}$ alkyl,
C$_{1-6}$ alkyl-C$_{3-7}$ cycloalkyl,
C$_{3-7}$ cycloalkyl,
aryl, wherein aryl is defined as phenyl or naphthyl, or
C$_{1-6}$ alkyl-aryl;

R$^3$ is:
C$_{1-6}$ alkyl,
C$_{1-6}$ alkyl-C$_{3-7}$ cycloalkyl,
C$_{3-7}$ cycloalkyl,
aryl, wherein aryl is defined as phenyl or naphthyl, or
C$_{1-6}$ alkyl-aryl;

R$^4$ is:
H,
C$_{1-6}$ alkyl,
C$_{1-6}$ alkyl-aryl, wherein aryl is unsubstituted or substituted with X, wherein X is defined as Br, Cl, F, I, or C$_{1-6}$ alkoxy, or
C$_{1-6}$ alkyl-1,1'-biphenyl, wherein the biphenyl is unsubstituted or substituted with an R$^7$ substituent, wherein R$^7$ is selected from the group consisting of:
CO$_2$H, CO$_2$R$^3$, 5-tetrazolyl, SO$_2$NHCOR$^5$, SO$_2$NHCO$_2$R$^5$;

R$^5$ is:
C$_{1-6}$ alkyl,
aryl, wherein aryl is defined as phenyl or naphthyl, or
C$_{1-6}$ alkyl-aryl;

which comprises the steps of:

(a) condensing

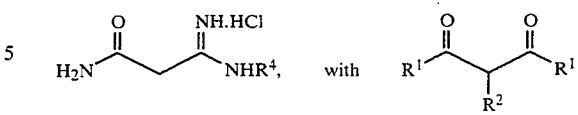

in a basic solution at a temperature range of about 25° C. (room temperature) to about 70° C. to produce a substituted pyridine

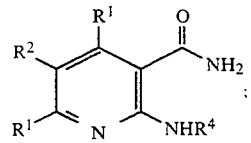

(b) reacting the substituted pyridine with

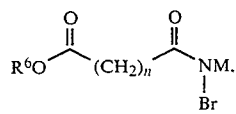

wherein:

R$^6$ is defined as M, H or C$_{1-6}$ alkyl;

M is defined a K$^+$, Na$^+$, Li$^+$, Cs$^+$, or Ba$^{+2}$;

n is 2 to 5; in an aqueous basic solution to produce a cyclic urea:

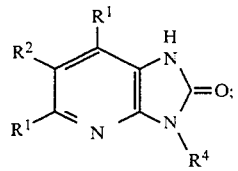

(c) heating the cyclic urea at a temperature range of between about 110° C. to about 180° C. in a solvent of R$^3$CO$_2$H and (R$^3$CO)$_2$O and a Lewis acid to produce the compound of formula I.

2. The process as recited in claim 1, for the preparation of a compound of formula I:

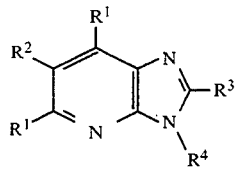

which comprises (a) condensing

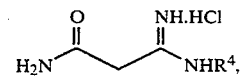

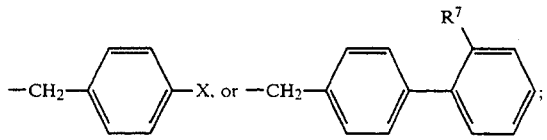

with

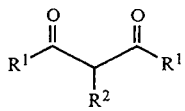

in a basic solution at a temperature range of about 25° C. (room temperature) to about 70° C. to produce a substituted pyridine:

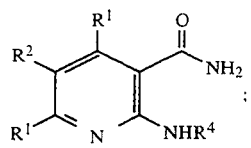

(b) reacting the substituted pyridine with

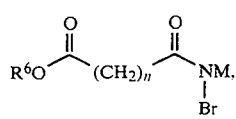

wherein:
 $R^6$ is defined as M, H or $C_{1-6}$ alkyl;
 M is defined a $K^+$, $Na^+$, $Li^+$, $Cs^+$, or $Ba^{+2}$;
 n is 2 to 5; in an aqueous basic solution to produce a cyclic urea:

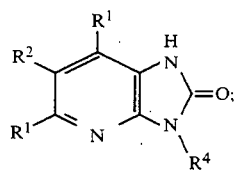

(c) heating the cyclic urea at a temperature range of between about 110° C. to about 180° C. in a solvent of $R^3CO_2H$ and $(R^3CO)_2O$ and a Lewis acid to produce the compound of formula I.

3. The process as recited in claim 1, for the preparation of a compound of formula Ia:

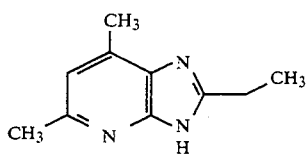

which comprises
 (a) condensing

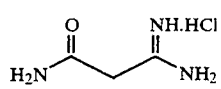

-continued with

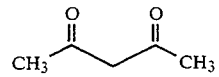

in a basic solution at a temperature range of about 25° C. (room temperature) to about 70° C. to produce a substituted pyridine

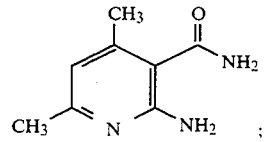

(b) reacting the substituted pyridine with

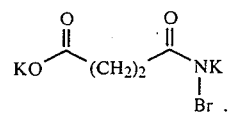

in an aqueous basic solution to produce a cyclic urea:

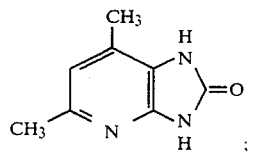

(c) heating the cyclic urea at a temperature range of between about 110° C. to about 180° C. in a solvent of $CH_3CH_2CO_2H$ and $(CH_3CH_2CO)_2O$ and $MgCl_2$ to produce the compound of formula Ia.

4. A process for the preparation of an imidazopyridine:

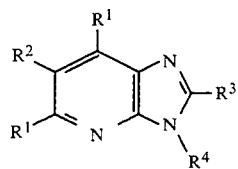

wherein:
 $R^1$ and $R^2$ are independently:
  H,
  $C_{1-6}$ alkyl,
  $C_{1-6}$ alkyl-$C_{3-7}$ cycloalkyl,
  $C_{3-7}$ cycloalkyl,
  aryl, wherein aryl is defined as phenyl or naphthyl, or
  $C_{1-6}$ alkyl-aryl;
 $R^3$ is:
  $C_{1-6}$ alkyl,
  $C_{1-6}$ alkyl-$C_{3-7}$ cycloalkyl,
  $C_{3-7}$ cycloalkyl,
  aryl, wherein aryl is defined as phenyl or naphthyl, or
  $C_{1-6}$ alkyl-aryl;
 $R^4$ is:

H, $C_{1-6}$ alkyl, $C_{1-6}$ alkyl-aryl, wherein aryl is unsubstituted or substituted with X, wherein X is defined as Br, Cl, F, I, or $C_{1-6}$ alkoxy, or $C_{1-6}$ alkyl-1,1'-biphenyl, wherein the biphenyl is unsubstituted or substituted with an $R^7$ substituent, wherein $R^7$ is selected from the group consisting of:

$CO_2H$, $CO_2R^3$, tetrazol-5-yl, $SO_2NHCOR^5$, $SO_2NHCO_2R^5$;

$R^5$ is:

$C_{1-6}$ alkyl, aryl, wherein aryl is defined as phenyl or naphthyl, or $C_{1-6}$ alkyl-aryl; comprising heating a cyclic urea

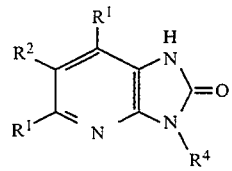

at a temperature range of between about 110° C. to about 180° C. in a solvent consisting essentially of $R^3CO_2H$ and $(R^3CO)_2O$ and a Lewis acid.

5. The process as recited in claim 4, for the preparation of a compound of formula I wherein the Lewis acid is selected from the group consisting of $MgCl_2$ or $MgSO_4$.

6. The process as recited in claim 5, for the preparation of

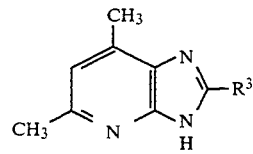

wherein the cyclic urea is

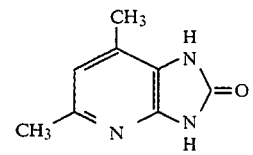

7. The process as recited in claim 6, for the preparation of a compound of formula I, wherein $R^3CO_2H$ and $(R^3CO)_2O$ are propionic acid and propionic acid anhydride.

8. The process as recited in claim 7, for the preparation of a compound of formula I, wherein Lewis acid is $MgCl_2$.

* * * * *

UNITED STATES PATENT AND TRADEMARK OFFICE
CERTIFICATE OF CORRECTION

PATENT NO. : 5,424,432
DATED : June 13, 1995
INVENTOR(S) : Laura E. Fredenburgh, et. al.

It is certified that error appears in the above-indentified patent and that said Letters Patent is hereby corrected as shown below:

Column 25, in Claim 2, lines 1-5 read:

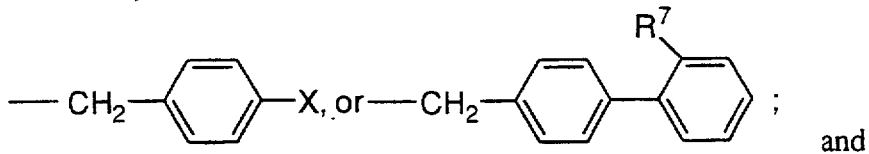

and should read:

wherein:

$R^4$ is 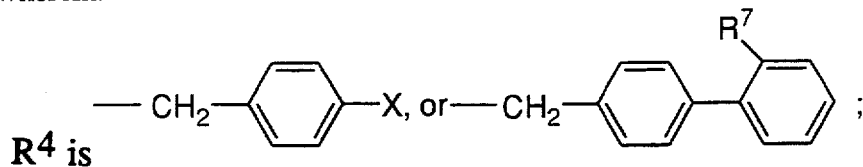

Signed and Sealed this

Twelfth Day of September, 1995

Attest:

BRUCE LEHMAN

*Attesting Officer*    *Commissioner of Patents and Trademarks*